United States Patent
Jermann et al.

(10) Patent No.: US 8,207,108 B2
(45) Date of Patent: Jun. 26, 2012

(54) STABILIZING COMPOSITION

(75) Inventors: Roland Jermann, Laufen (CH);
Caroline Ploton, Saint Louis (FR);
Horst Westenfelder, Neustadt a. d.W. (DE)

(73) Assignee: DSM IP Assets B.V., Heerlen (NL)

( * ) Notice: Subject to any disclaimer, the term of this patent is extended or adjusted under 35 U.S.C. 154(b) by 518 days.

(21) Appl. No.: 12/096,067

(22) PCT Filed: Nov. 27, 2006

(86) PCT No.: PCT/EP2006/011327
§ 371 (c)(1),
(2), (4) Date: Aug. 20, 2008

(87) PCT Pub. No.: WO2007/065575
PCT Pub. Date: Jun. 14, 2007

(65) Prior Publication Data
US 2008/0318833 A1 Dec. 25, 2008

(30) Foreign Application Priority Data
Dec. 9, 2005 (EP) .................................. 05026932

(51) Int. Cl.
*A61K 8/00* (2006.01)
*C08L 95/00* (2006.01)
(52) U.S. Cl. .................................. 512/2; 512/1; 424/59
(58) Field of Classification Search .................. 512/1, 2; 424/59
See application file for complete search history.

(56) References Cited

U.S. PATENT DOCUMENTS

| 5,676,934 A | 10/1997 | Siegfried |
| 6,015,548 A | 1/2000 | Siddiqui et al. |
| 7,001,592 B1 * | 2/2006 | Traynor et al. ................. 424/59 |
| 2003/0039619 A1 | 2/2003 | Bunger et al. |
| 2004/0126336 A1 * | 7/2004 | Hansenne et al. .............. 424/59 |

FOREIGN PATENT DOCUMENTS

| AU | B-731505/91 | * | 2/1991 |
| EP | 0 780 119 | | 6/1997 |
| WO | 99/33439 | | 7/1999 |
| WO | 2005/042828 | | 5/2005 |

OTHER PUBLICATIONS

MSDS ethylhexyl salicylate or OCTYL SALICYLATE Oxford University UK http://msds.chem.ox.ac.uk/ET/2-ethylhexyl_salicylate.html.*
International Search Report for PCT/EP2006/011327 mailed Mar. 29, 2007.
Written Opinion for PCT/EP2006/011327 mailed Mar. 29, 2007.

* cited by examiner

*Primary Examiner* — Patrick Joseph Ryan
*Assistant Examiner* — Aaron Greso
(74) *Attorney, Agent, or Firm* — Nixon & Vanderhye P.C.

(57) ABSTRACT

The present invention relates to compositions of UV absorbers and optionally additional antioxidants. The compositions are useful for the protection and stabilization of photosensitive ingredients such as colorants, dyes, scents, fragrances and active ingredients in body care products, household products or inks against the deleterious effects of ultraviolet radiation and oxygen.

9 Claims, No Drawings

STABILIZING COMPOSITION

This application is the U.S. national phase of International Application No. PCT/EP2006/011327 filed 27 Nov. 2006 which designated the U.S. and claims priority to European Patent Application No. 05026932.3 filed 9 Dec. 2005, the entire contents of each of which are hereby incorporated by reference.

The present invention relates to compositions of UV absorbers and optionally additional antioxidants. The compositions are useful for the protection and stabilization of photosensitive ingredients such as colorants, dyes, scents, fragrances and active ingredients in body care products, household products or inks against the deleterious effects of ultraviolet radiation and oxygen.

It has been found that a composition of UV absorbers, optionally in combination with an antioxidant is especially effective for stabilization against such deleterious effects when incorporated into these products.

For commercial success of a consumer product a pleasant appearance and a fresh smell is today mandatory. In order to make this immediately apparent, sophisticated products containing new fragrances and active ingredients in colorful formulations are often displayed in transparent or slightly colored packaging. However, within such packaging the products are often exposed to ultraviolet irradiation and oxygen which can result in decomposition processes destroying the pleasant product appearance, active ingredients and fragrance leading to unwanted color changes, unpleasant off-odors and loss of performance.

Various stabilization techniques of clear package products by absorption of UV light are commonly used and well known. For example UV-light absorber such as benzophenone or benzotriazole derivatives are used to enhance the products stability and shelf life due to their absorption properties. However, these compounds are solids having a very limited solubility. This feature makes their incorporation into the desired product form often very difficult as the UV-light absorber often tend to re-crystallization in the final product form. This consequently reduces the protection properties as well as the aesthetic appearance of the product and is thus highly unwanted. Benzophenone derivatives which are widely used as stabilizer for product protection against UV-radiation mainly absorb in the UV-B range and are therefore not able to completely inhibit the decomposition of photosensitive ingredients such as colorants, dyes, scents, fragrances or active compounds and mixtures thereof. Additionally, complex mixtures of UV-filters, hindered nitroxyl and hydroxylamine compounds are described for the stabilization as e.g. in WO 2005/042828.

A good stabilizer for efficient protection against the deleterious effects of light and oxygen should be easily accessible, have an excellent cost/performance ratio, have excellent UV-A as well as UV-B filter activity, show a good photo stability, excellent heat stability, very good solubility while preferably being liquid, compatibility with cosmetic bases, pH stability in the range of 4 to 9, processability into a variety of products such as body care products, household products or inks, compatibility with other ingredients and with the packaging materials and should be free of color and be of neutral or pleasant odor and have a low volatility.

4,4'-Methoxy-tert.butyldibenzoylmethane (INCI: avobenzone, e.g. commercially available as PARSOL® 1789) is well known to have a limited photo-stability and solubility but at the same time excellent UV-A protection abilities. Thus, the incorporation of 4,4'-Methoxy-tert.butyldibenzoylmethane alone as stabilizer is not suitable as it would decompose upon irradiation. Additionally, 4,4'-Methoxy-tert.butyldibenzoylmethane is known to interact with other conventionally used UV-filters such as ethylhexyl methoxycinnamate. Thus, such combinations would not be favorable.

Homomethylsalicylate (INCI: Homosalate, e.g. commercially available as PARSOL® HMS) and 2-ethylhexyl 2-cyano-3,3-diphenylacrylate (INCI: Octocrylene e.g. commercially available as PARSOL® 340), the preferred 2-cyano 3,3-diphenylacrylate according to the invention, itself are poor UV-B absorber with low extinction coefficients and are on their own not suited for the effective stabilization of photosensitive ingredients.

It has now been found that a composition of organic UV absorbers, optionally in combination with an oil soluble antioxidant and further optionally with other usual cosmetic additives or mixtures thereof (in the following referred to as stabilizing composition) overcomes the shortcomings of the prior art and is thus suitable to stabilize photosensitive ingredients such as colorants, dyes, scents, fragrances and active ingredients or mixtures thereof in body care products, household products or inks against the deleterious effects of UV-A and UV-B radiation and oxygen. As this composition is liquid it can be easily incorporated into all classes of body care and household products as well as into inks.

Thus in one embodiment, the present invention relates to a stabilizing composition comprising at least 10 wt. % of 4,4'-Methoxy-tert.butyldibenzoylmethane, preferably 10-20 wt. % at least 50 wt. % of 2-Cyano-3,3-diphenylacrylate, preferably 50-70 wt. % at least 15 wt. % of Homomethylsalicylate, preferably 15-30 wt. % and, optionally, an oil soluble antioxidant, preferably 0.5-5 wt. % and, further optionally, other usual cosmetic additives whereas the sum of the ingredients is 100%.

2-Cyano-3,3-diphenylacrylate encompasses all esters of 2-Cyano-3,3-diphenylacrylic acid. Such esters include linear or branched C1 to C 10 alkyl ester (e.g. methyl, ethyl, propyl, isopropyl, butyl, sec. butyl, isobutyl, pentyl, neopentyl, hexyl, 2-ethyl-hexyl, and octyl esters), C3-C8 cycloalkyl esters (e.g. cyclopropyl, cyclobutyl, cyclopentyl, cyclohexyl, cycloheptyl or cyclooctyl esters) and the like. In all embodiments of the invention the preferred 2-Cyano-3,3-diphenylacrylate are ethyl 2-cyano-3,3-diphenylacrylate (INCI: etocrylene) and 2-ethylhexyl 2-cyano-3,3-diphenylacrylate (INCI Octocrylene). The most preferred 2-Cyano-3,3-diphenylacrylate is 2-ethylhexyl 2-cyano-3,3-diphenylacrylate.

Examples of oil soluble antioxidants are butylated hydroxytoluene (BHT), ascorbylpalmitate, butylated hydroxyanisole, α-tocopherol, mixed tocopherol, natural tocopherol, phenyl-α-naphtylamine or mixtures thereof without being limited thereto.

The term mixed tocopherol refers to a mixture of α-, β-, γ-, and δ-tocopherol, eventually dissolved in an oil such as plant oil. Natural tocopherol can be obtained from soy or wheat and normally comprises α-, β-, γ-, and δ-tocopherol eventually dissolved in an oil such as plant oil. Such products are e.g. available as Dermofeel® Toco 70 by drstraetmans or Mixed Tocopherols by DSM Nutritional products.

Examples of usual cosmetic additives are fatty substances, oils, organic solvents, silicones, thickeners, softeners, emulsifiers, antifoaming agents, moisturizers, fragrances, surfactants, anionic, cationic, nonionic or amphoteric polymers or mixtures thereof.

A more preferred embodiment of the stabilizing composition comprises
at least 12 wt. % of 4,4'-Methoxy-tert.butyldibenzoylmethane, preferably 12-17 wt. %
at least 50 wt. % of 2-Cyano-3,3-diphenylacrylate, preferably 55-65 wt. %
at least 15 wt. % of Homomethylsalicylate, preferably 18-25 wt. %
and, optionally, mixed or natural tocopherol, preferably 0.5-5 wt. % thereof
and, further optionally, other usual cosmetic additives
whereas the sum of the ingredients is 100%.

Most preferred is a stabilizing composition consisting of
15 wt. % of 4,4'-Methoxy-tert.butyldibenzoylmethane
60 wt. % of 2-Cyano-3,3-diphenylacrylate
23 wt. % of Homomethylsalicylate
And 2 wt. % of mixed or natural tocopherol.

The present invention also pertains to body care products, household products or inks, in particular to body care products and household products containing an effective stabilizing amount of a stabilizing composition as defined earlier. Preferably, the body care product is a perfume or a toilet water such as an eau de Cologne, an eau de Toilette, an eau de Perfume or a perfume or an extrait containing an effective amount of the stabilizing composition according to the invention. Even more preferably, the perfume or toilet water contains about 60-90 wt.-% of ethanol, even more preferably about 75-85 wt.-% of ethanol.

Within the scope of the invention, the term "effective amount" or "effective stabilizing amount" means generally at least a concentration of 0.02% by weight based on the total formulation i.e. based on the total weight of the body care product, the household product or the ink. Preferably, a concentration of 0.05-1 wt. %, most preferred of 0.05-0.5 wt. % based on the total weight of the body care product, the household product or the ink the is used.

The stabilizing composition according to the invention is particularly suitable for stabilizing photosensitive colorants, dyes, scents, fragrances or active ingredients or mixtures thereof in body care products and household products. Preferably, the active ingredient is selected from vitamins, carotenoids, vegetable extract, antibacterials, ubiquinones, phenols, polyphenols or flavonoids.

Thus, in another embodiment, the invention relates to the use of a stabilizing composition according to the invention for the stabilization of colorants, dyes, scents, fragrances, active ingredients or mixtures thereof in body care products and household products. Preferably, the invention relates to the use of a stabilizing composition according to the invention for the stabilization of colorants, dyes, scents, fragrances or mixtures thereof. Even more preferably the invention relates to the use of a stabilizing composition according to the invention for the stabilization of colorants, dyes, scents, fragrances or mixtures thereof in clear liquid or gel-like preparations such as perfumes, toilet waters, liquid soaps, detergents and the like. For the use according to the invention an effective amount as defined above of the stabilizing composition is used.

Furthermore the invention relates to a method for the stabilization of colorants, dyes, scents, fragrances, active ingredients or mixtures thereof in body care products and household products which method comprises the addition of an effective stabilizing amount of a stabilizing composition according to the invention to the body care product and household product. Preferably the active ingredient is selected from vitamins, carotenoids, vegetable extract, antibacterials, ubiquinones, phenols, polyphenols or flavanoids. Preferably, the effective stabilizing amount is within a concentration range of 0.05-0.5 wt. % based on the total weight of the product.

In another embodiment of the invention the stabilizing composition is also suitable for stabilizing photosensitive colorants and dyes as used in inks which are used e.g. for ink jet printing, pencils, markers or endorsing inks are dye-based or pigment based. These inks and consequently e.g. inkjet prints made with these inks are susceptible to light fading as the colorants photodegrade upon irradiation, especially with UV light. Surprisingly, it has been found that the stabilizing composition according to the invention is especially suitable for inhibiting the photodegradation of dyes, colorants or pigments used in inks leading to an increased lightfastness. The amount used of the stabilizing composition according to the invention for the protection of inks is at least 0.01 wt. %, preferably in the in the range of 0.05-5 wt. %, most preferred in the range of 0.05-3 wt. %.

Generally, for the coloration of household products, body care products and inks all substances are suitable which have an absorption in the visible light of electromagnetic radiation (400-4000 nm) The absorption is often caused by the following chromophores: Azo- (mono-, di-, tris, or poly-)stilbene-, carotenoide-, diarylmethan-, triarylmethan-, xanthene-, acridine-, quinoline-, methin- (also polymethin-) thiazol-, indamine-, indophenol-, azin-, oxazin-, thiazin-, anthraquinone- indigo-, phthalocyanin and further synthetic, natural and/or inorganic chromophores.

FD&C and D&C colorants which can be stabilized with the stabilizing composition according to the invention are e.g. curcumin, riboflavin, lactoflavin, tartrazine, chinolinyellow, cochenille, azorubin, amaranth, ponceau 4R, erythrosine, red 2G, indigotin, chlorophyll, chlorophyllin, caramel, carbo medicinalis, carotenoids, carotin, bixin, norbixin, annatto, orlean, capsanthin, capsorubin, lycopin, xanthophyll, flavoxanthin, lutein, kryptoaxanthin, rubixanthin, violaxanthin, rhodoxanthin, canthaxanthin, betanin, anthocyans without being limited thereto. Dyes which can be stabilized according to the inventions are e.g. inorganic pigments such as iron oxide (iron oxide red, iron oxide yellow, iron oxide black etc.) ultramarines, chromium oxide green or carbon black. Other colorants and dyes which can be stabilized with the stabilizing composition according to the invention comprise natural or synthetic organic pigments, disperse dyes which may be solubilized in solvents like direct hair dyes of the HC type, for example HC red No. 3, HC Blue No. 2 and all other hair dyes listed in International Cosmetic Ingredient Dictionary Handbook 7$^{th}$ edition 1997) or the dispersion dyes listed in Color Index International Society of Dyers and Colorist, color varnishes (insoluble salts of soluble dyes, like many Ca-, Ba- or Al-salts of anionic dyes), soluble anionic or cationic dyes such as acid dyes (anionic), basic dyes (cationic), direct dyes, reactive dyes or solvent dyes, fluorescent dyes, fluorescein and isothiocyanates.

Scents and fragrances used in body care products and household products which can be stabilized with the stabilizing composition according to the invention comprise at least one, preferably numerous odorant ingredients of natural and/or synthetic origin. The range of the natural odorants includes, in addition to readily volatile, also moderately and only slightly volatile components. The synthetic odorants embrace representatives from practically all classes of odorant substances.

The following list comprises examples of known odorants which may be stabilized with the stabilizing composition according to the invention without being limited thereto: natural products such as tree moss absolute, basil oil, tropical fruit oils (such as bergamot oil, mandarin oil, etc.), mastix absolute, myrtle oil, palmarosa oil, patchouli oil, petitgrain oil, wormwood oil, lavender oil, rose oil, jasmine oil, ylang-ylang oil, etc.; alcohols: farnesol, geraniol, linalool, nerol, phenylethyl alcohol, rhodinol, cinnamic alcohol, (Z)-hex-3-en-1-ol, menthol, a-terpineol, etc.; aldehydes such as citral, alpha-hexyl cinnamaldehyde, Lilial, methylionone, verbenone, nootkatone, geranylacetone, etc.; esters such as allyl phenoxyacetate, benzyl salicylate, cinnamyl propionate, citronellyl acetate, decyl acetate, dimethylbenzylcarbinyl acetate, dimethylbenzylcarbinyl butyrate, ethyl acetoacetate, cis-3-hexenyl isobutyrate, cis-3-hexenyl salicylate, linalyl acetate, methyl dihydrojasmonate, styralyl propionate, vetiveryl acetate, benzyl acetate, geranyl acetate, etc.; lactones such as gamma-undecalactone, delta-decalactone, pentadecanolide, 12-oxahexadecanolide, etc.; acetals such as Viridine (phenylacetaldehyde dimethylacetal), etc.; and other components often used in perfumery such as indole, p-mentha-8-thiol-3-one, methyleugenol, eugenol, anethol, etc.

Active ingredients used in body care products and household products which can be stabilized with the stabilizing composition according to the invention comprises vitamins such as tocopherol, ascorbic acid, ascorbyl phosphate, vitamin Q, D, and K, retinol, retinal, retinoic acid, retinol acetate, retinol palmitate, carotinoid derivatives such as beta carotene, lycopene, asthaxanthene, vegetable extracts, antibacterial ingredients, instable amino acids comprising dipeptides, oligopeptides and polypeptides such as methionen, cystein, cystin, tryptophan, phenylalanine, tyrosin, phenols, polyphenols or flavanoids, bisabolol, allantoin, phytantriol, panthenol, AHA acids, Ubichinones such as Coenzym Q 10, ceramides, pseudoceramides, essential oils, plant extracts deoxyribonucleic acid.

Body-care products according to the invention are skin care preparations, preparations containing scents and/or fragrances, hair-care preparations, dentrifices, deodorant and antiperspirant, decorative preparations, light protection preparations and functional preparations. Preferred body care products are skin care preparations, preparations containing scents and/or fragrances, hair-care preparations and decorative preparations.

Examples of skin care preparations are, in particular, body oils, body lotions, body gels, treatment creams, skin protection ointments, shaving preparations, such as shaving foams or gels, skin powders such as baby powder, moisturizing gels, moisturizing sprays, revitalizing body sprays, cellulite gels, anti acne preparations and peeling preparations.

Preparations containing scents and/or fragrances are in particular perfumes, toilet waters and shaving lotions (aftershave preparations).

Examples of hair care products are, for example, shampoo for humans and animals, hair conditioners, products for styling and treating hair, perming agents, hair sprays and lacquers, hair gels, hair fixatives and hair dying or bleaching agents.

Examples of dentifrices are in particular tooth cream, toothpastes, mouth-washes, mouth rinses, anti-plaque preparations and cleansing agents for dentures.

Examples of decorative preparations are in particular lipstick, nail varnishes, eye shadow, mascaras, dry and moist make-up, rouge, powders, depilatory agents, and suntan lotions.

Examples of functional preparations are cosmetic or dermatological compositions containing active ingredients such as hormone preparations, vitamin preparations, vegetable extract preparations and antibacterial preparations.

Body care products in accordance with the invention such as cosmetic and dermatological compositions can be in the form of a liquid, lotion, a thickened lotion, a gel, a cream, a milk, an ointment, a paste, a powder, a make-up, or a solid tube stick and can be optionally be packaged as an aerosol and can be provided in the form of a mousse, foam or a spray foams, sprays, sticks or aerosols or wipes.

The body care products according to the invention can be in the form of a suspension or dispersion in solvents or fatty substances, or alternatively in the form of an emulsion or micro emulsion (in particular of O/W or W/O type, O/W/O or W/O/W-type), such as a cream or a milk, a vesicular dispersion, in the form of an ointment, a gel, a solid tube stick or an aerosol mousse. The emulsions can also contain anionic, nonionic, cationic or amphoteric surfactant.

The stabilizing composition according to the invention may be present in the oil or in the aqueous or aqueous ethanolic phase. Preferably, the stabilizing composition is incorporated into the oil or into the aqueous ethanolic phase.

The body care products or household products according to the invention can also contain usual adjuvants and additives, such as preservatives/antioxidants, fatty substances/oils, water, organic solvents, silicones, thickeners, softeners, emulsifiers, additional screening agents, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, light stabilizers, insect repellants, skin tanning agents, skin whitening agents, antibacterial agents, preservatives or any other ingredients usually formulated into cosmetics. The necessary amounts of the cosmetic and dermatological adjuvants and additives can, based on the desired product, easily be chosen by a skilled artisan in this field and will be illustrated in the examples, without being limited hereto.

Additional screening agents are advantageously selected from the compounds listed below without being limited thereto:

Examples of UV-B or broad spectrum screening agents, i.e. substances having absorption maximums between about 290 and 340 nm, which come into consideration for combination with the compounds of the present invention are for example the following organic and inorganic compounds: Acrylates such as 2-ethylhexyl 2-cyano-3,3-diphenylacrylate (octocrylene, PARSOL® 340), ethyl 2-cyano-3,3-diphenylacrylate and the like; Camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like; Cinnamate derivatives such as octyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes; p-Aminobenzoic acid derivatives, such as p-aminobenzoic acid, 2-ethylhexyl p-dimethylaminobenzoate, N-oxypropylenated ethyl p-aminobenzoate, glyceryl p-aminobenzoate, Benzophenones such as benzophenone-3, benzophenone-4, 2,2',4,4'-tetrahydroxy-benzophenone, 2,2'-dihydroxy-4,4'-dimethoxybenzophenone and the like; Esters of Benzalmalonic acid such as di-(2-ethylhexyl)4-methoxybenzalmalonate; Esters of 2-(4-ethoxy-anilinomethylene) propandioic acid such as 2-(4-ethoxy anilinomethylene)propandioic acid diethyl ester as described in the European Patent Publication EP 0895 776; Organosiloxane compounds containing benzmalonate groups as described in the European Patent Publications EP 0358584 B1, EP 0538431 B1 and EP 0709080 A1; Drometrizole trisiloxane (Mexoryl XL); Pigments such as microparticulated $TiO_2$, and the like. The term "microparticulated" refers to a particle size from about 5 nm to about 200 nm, particularly from about 15 nm to about 100 nm. The $TiO_2$ particles may also be coated by metal oxides such as e.g. aluminum or zirconium oxides or by organic coatings such as e.g. polyols, methicone, aluminum stearate, alkyl silane. Such coatings are well known in the art. Imidazole derivatives such as e.g. 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanolamine salts, diethanolamine salts and the like. Salicylate derivatives such as isopropylbenzyl salicylate, benzyl salicylate, butyl salicylate, octyl salicylate (NEO HELIOPAN OS), isooctyl salicylate or homomethyl salicylate (homosalate, HELIOPAN) and the like. Triazine derivatives such as octyl triazone (UVINUL T-150), dioctyl butamido triazone (UVASORB HEB), bis ethoxyphenol methoxyphenyl triazine (Tinosorb S) and the like. Examples of broad spectrum or UV A screening agents i.e. substances having absorption maximums between about 320 and 400 nm, which come into consideration for combination with the compounds of the present invention are for example the following organic and inorganic compounds: Dibenzoylmethane derivatives such as 4-tert. butyl-4'-methoxydibenzoyl-methane (PARSOL® 1789), dimethoxydibenzoylmethane, isopropyldibenzoylmethane and the like; Benzotriazole derivatives such as 2,2'-methylene-bis-(6-(2H-benzotriazole-2-yl)-4-(1,1,3,3,-tetramethylbutyl)-phenol (TINOSORB M) and the like; Phenylene-1,4-bis-benzimidazolsulfonic acids or salts such as 2,2-(1,4-phenylene)bis-(1H-benzimidazol-4,6-disulfonic acid) (Neoheliopan AP); Amino substituted hydroxybenzophenones such as 2-(4-Diethylamino-2-hydroxy-benzoyl)-benzoic acid hexylester (Uvinul A plus) as described in the European Patent Publication EP 1046391; Pigments such as microparticulated ZnO or $TiO_2$ and the like. The term "microparticulated" refers to a particle size from about 5 nm to about 200 nm, particularly from about 15 nm to about 100 nm. The particles may also be coated by other metal oxides such as e.g. aluminum or zirconium oxides or by organic coatings such as e.g. polyols, methicone, aluminum stearate, alkyl silane. Such coatings are well known in the art.

As dibenzoylmethane derivatives have limited photostability it may be desirable to photostabilize these UV-A screening agents. Thus, the term "conventional UV-A screening agent" also refers to dibenzoylmethane derivatives such as e.g. PARSOL® 1789 stabilized by, e.g., 3,3-Diphenylacrylate derivatives as described in the European Patent Publications EP 0 514 491 B1 and EP 0 780 119 A1; Benzylidene camphor derivatives as described in the U.S. Pat. No. 5,605,680; Organosiloxanes containing benzmalonate groups as described in the European Patent Publications EP 0358584 B1, EP 0538431 B1 and EP 0709080 A1.

Based on the invention all known antioxidants usually formulated into body care, household and fragrance products can be used. Especially preferred are antioxidants chosen from the group consisting of amino acids (e.g. glycine, histidine, tyrosine, tryptophan) and their derivatives, imidazole (e.g. urocanic acid) and derivatives, peptides such as D,L-carnosine, D-carnosine, L-carnosine and derivatives (e.g. anserine), carotenoids, carotenes (e.g. α-carotene, β-carotene, lycopene) and derivatives, chlorogenic acid and derivatives, lipoic acid and derivatives (e.g. dihydrolipoic acid), aurothioglucose, propylthiouracil and other thiols (e.g. thioredoxine, glutathione, cysteine, cystine, cystamine and its glycosyl-, N-acetyl-, methyl-, ethyl-, propyl-, amyl-, butyl- and lauryl-, palmitoyl-; oleyl-, γ-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthioninsulfoximine, homocysteinesulfoximine, buthioninsulfone, penta-, hexa-, heptathioninsulfoximine) in very low compatible doses (e.g. pmol bis μmol/kg), additionally (metal)-chelators (such as α-hydroxyfatty acids, palmic-, phytinic acid, lactoferrin), β-hydroxyacids (such as citric acid, lactic acid, malic acid), huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamin C and derivatives (such as ascorbylpalmitate and ascorbyltetraisopalmitate, Mg-ascorbylphosphate, Na-ascorbylphosphate, ascorbyl-acetate), tocopherol and derivates (such as vitamin-E-acetate), mixtures of nat. vitamin E, vitamin A and derivatives (vitamin-A-palmitate and -acetate) as well as coniferylbenzoate, rutinic acid and derivatives, α-glycosylrutin, ferulic acid, furfurylideneglucitol, carnosine, butylhydroxytoluene, butylhydroxyanisole, trihydroxybutyrophenone, urea and its derivatives, mannose and derivatives, zinc and derivatives (e.g. ZnO, $ZnSO_4$), selen and derivatives (e.g. selenomethionin), stilbenes and derivatives (such as stilbenoxide, trans-stilbenoxide) and suitable derivatives (salts, esters, ethers, sugars, nucleotides, nucleosides, peptides and lipids) of the named active ingredients. One or more preservatives/antioxidants may be present in an amount of at least 0.01 wt. % of the total weight of the composition. Preferably about 0.01 wt. % to about 10 wt. % of the total weight of the composition of the present invention is present. Most preferred, one or more preservatives/antioxidants are present in an amount about 0.1 wt. % to about 1 wt. %.

Typically formulations also contain surface active ingredients like emulsifiers, solubilizers and the like. An emulsifier enables two or more immiscible components to be combined homogeneously. Moreover, the emulsifier acts to stabilize the composition. Emulsifiers that may be used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polygylceryl-4-oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further exemplary emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glycerides phosphate and mixtures thereof. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof. The preferred emulsifiers are cetyl phosphate (Amphisol® A), diethanolamine cetyl phosphate (Amphisol®), potassium cetyl phosphate (Amphisol® K), PVP Eicosene copolymer, acrylates/$C_{10-30}$-alkyl acrylate crosspolymer, PEG-20 sorbitan isostearate, sorbitan isostearate, and mixtures thereof. The one or more emulsifiers are present in a total amount of at least 0.01 wt. % of the total weight of the composition. Preferably about 0.01 wt. % to about 20 wt. % of the total weight of the composition of the present invention is used. Most preferred, about 0.1 wt. % to about 10 wt. % of emulsifiers are used.

The lipid phase can advantageously be chosen from: mineral oils and mineral waxes; oils such as triglycerides of caprinic acid or caprylic acid, preferable castor oil; oils or waxes and other natural or synthetic oils, in an preferred embodiment esters of fatty acids with alcohols e.g. isopropanol, propyleneglycol, glycerin or esters of fatty alcohols with carbonic acids or fatty acids; alkylbenzoates; and/or silicone oils such as dimethylpolysiloxane, diethylpolysiloxane, diphenylpolysiloxane, cyclomethicones and mixtures thereof.

Exemplary fatty substances which can be incorporated in the oil phase of the emulsion, microemulsion, oleo gel, hydrodispersion or lipodispersion of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters can advantageously be selected from octylpalmitate, octylcocoate, octylisostearate, octyldodecylmyristate, cetearylisononanoate, isopropylmyristate, isopropylpalmitate, isopropylstearate, isopropyloleate, n-butylstearate, n-hexyl-laureate, n-decyloleate, isooctylstearate, isononylstearate, isononylisononanoate, 2-ethyl hexylpalmitate, 2-ethylhexyl-laurate, 2-hexyldecylstearate, 2-octyldodecylpalmitate, stearylheptanoate, oleyloleate, oleylerucate, erucyloleate, erucylerucate, tridecylstearate, tridecyltrimellitate, as well as synthetic, half-synthetic or natural mixtures of such esters e.g. jojoba oil.

Other fatty components suitable for use in the formulation of the present invention include polar oils such as lecithins and fatty acid triglycerides, namely triglycerol esters of saturated and/or unsaturated, straight or branched carboxylic acid with 8 to 24 carbon atoms, preferably of 12 to 18 carbonatoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes e.g. mineral oils, vaseline (petrolatum); paraffins, squalane and squalene, polyolefins, hydrogenated polyisobutenes and isohexadecanes, favored polyolefins are polydecenes; dialkyl ethers such as dicaprylylether; linear or cyclic silicone oils such as preferably cyclomethicone (octamethylcyclotetrasiloxane; cetyldimethicone, hexamethylcyclotrisiloxane, polydimethylsiloxane, poly(methylphenylsiloxane) and mixtures thereof.

Other fatty components which can advantageously be incorporated in formulations of the present invention are isoeikosane; neopentylglycoldiheptanoate; propyleneglycol-dicaprylate/dicaprate; caprylic/capric/diglycerylsuccinate; butyleneglycol caprylat/caprat; $C_{12-13}$-alkyllactate; di-$C_{12-13}$-alkyltartrate; triisostearin; dipentaerythrityl hexacaprylat/hexacaprate; propyleneglycolmonoisostearate; tricaprylin; dimethylisosorbid. Especially beneficial is the use of mixtures $C_{12-15}$-alkylbenzoate and 2-ethylhexylisostearate, mixtures $C_{12-15}$-alkylbenzoate and isotridecylisononanoate as well as mixtures of $C_{12-15}$-alkylbenzoate, 2-ethylhexylisostearate and isotridecylisononanoate.

The oily phase of the formulation of the present invention can also contain natural vegetable or animal waxes such as bee wax, china wax, bumblebee wax and other waxes of insects as well as shea butter and cocoa butter.

A moisturizing agent may be incorporated into a product of the present invention to maintain hydration or rehydrate the skin. Moisturizers that prevent water from evaporating from the skin by providing a protective coating are called emollients. Additionally an emollient provides a softening or soothing effect on the skin surface and is generally considered safe for topical use. Preferred emollients include mineral oils, lanolin, petrolatum, capric/caprylic triglyceraldehydes, cholesterol, silicones such as dimeticone, cyclometicone, almond oil, jojoba oil, avocado oil, castor oil, sesame oil, sunflower oil, coconut oil and grape seed oil, cocoa butter, olive oil aloe extracts, fatty acids such as oleic and stearic, fatty alcohols such as cetyl and hexadecyl (ENJAY), diisopropyl adipate, hydroxybenzoate esters, benzoic acid esters of $C_{9-15}$-alcohols, isononyl iso-nonanoate, ethers such as polyoxypropylene butyl ethers and polyoxypropylene cetyl ethers, and $C_{12-15}$-alkyl benzoates, and mixtures thereof. The most preferred emollients are hydroxybenzoate esters, aloe vera, $C_{12-15}$-alkyl benzoates, and mixtures thereof. An emollient is present in an amount of about 1 wt. % to about 20 wt. % of the total weight of the product. The preferred amount of emollient is about 2 wt. % to about 15 wt. %, and most preferably about 4 wt. % to about 10 wt. %.

Moisturizers that bind water, thereby retaining it on the skin surface are called humectants. Examples of humectants which can be incorporated into a product of the present invention are glycerin, polypropylene glycol, polyethylene glycol, lactic acid, pyrrolidone carboxylic acid, urea, phospholipids, collagen, elastin, ceramides, lecithin sorbitol, PEG-4, and mixtures thereof. Additional suitable moisturizers are polymeric moisturizers of the family of water soluble and/or swellable/and/or with water gelating polysaccharides such as hyaluronic acid, chitosan and/or a fucose rich polysaccharide which is e.g. available as Fucogel®1000 (CAS-Nr. 178463-23-5) by SOLABIA S. One or more humectants are optionally present at about 0.5 wt. % to about 8 wt. % in a product of the present invention, preferably about 1 wt. % to about 5 wt. %.

The aqueous phase of the products of the present invention can contain the usual cosmetic additives such as alcohols, especially lower alcohols, preferably ethanol and/or isopropanol, low diols or polyols and their ethers, preferably propyleneglycol, glycerin, ethyleneglycol, ethyleneglycol monoethyl- or monobutylether, propyleneglycol monomethyl- or -monoethyl- or -monobutylether, diethyleneglycol monomethyl- or monoethylether and analogue products, polymers, foam stabilizers; electrolytes and especially one or more thickeners. Thickeners that may be used in formulations of the present invention to assist in making the consistency of a product suitable include carbomer, siliciumdioxide, magnesium and/or aluminum silicates, beeswax, stearic acid, stearyl alcohol polysaccharides and their derivatives such as xanthan gum, hydroxypropyl cellulose, polyacrylamides, acrylate crosspolymers preferably a carbomer, such as carbopolea of type 980, 981, 1382, 2984, 5984 alone or mixtures thereof. Examples of neutralizing agents which may be included in the product of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginine and lysine and any combination of any foregoing. The neutralizing agent can be present in an amount of about 0.01 wt. % to about 8 wt. % in the product of the present invention, preferably, 1 wt. % to about 5 wt. %.

The addition of electrolytes into the product of the present invention may be necessary to change the behavior of a hydrophobic emulsifier. Thus, the emulsions/microemulsions of this invention may contain preferably electrolytes of one or several salts including anions such as chloride, sulfates, carbonate, borate and aluminate, without being limited thereto. Other suitable electrolytes can be on the basis of organic anions such as, but not limited to, lactate, acetate, benzoate, propionate, tartrate and citrate. As cations preferably ammonium, alkylammonium, alkali- or alkaline earth metals, magnesium-, iron- or zinc-ions are selected. Especially preferred salts are potassium and sodium chloride, magnesium sulfate, zinc sulfate and mixtures thereof. Electrolytes can be present in an amount of about 0.01 wt. % to about 8 wt. % in the product of the present invention. The addition of further light stabilizers may be desirable. Such light stabilizers are e.g. known as sterically hindered amine light stabilizer (HALS) which can be of monomeric or polymeric nature. They are for example selected from the group consisting of N,N'-bisformyl-N,N'-bis-(2,2,6,6-tetramethyl-4-piperidinyl)-hexamethylenediamine (Uvinul 4050H), bis-(2,2,6,6-tetramethyl-4-piperidyl)sebacate (Uvinul 4077H), (bis-(1,2,2,6,6-pentamethyl-4-piperidyl)-sebacate+methyl-(1,2,2,6,6-pentamethyl-4-piperidyl)sebacate. (Uvinul 4092H), bis(2,2,6,6-tetramethylpiperidin-4-yl)sebacate, bis (2,2,6,6-tetramethylpiperidin-4-yl)succinate, bis(1,2,2,6,6-pentamethylpiperidin-4-yl)sebacate, n-butyl-3,5-di-tert-butyl-4-hydroxybenzyl-malonic acid bis(1,2,2,6,6-pentamethylpiperidyl) ester, the condensate of 1-hydroxyethyl-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-s-triazine, tris(2,2, 6,6-tetramethyl-4-piperidyl)nitrilotriacetate, tetrakis(2,2,6,6-tetramethyl-4-piperidyl)-1,2,3,4-butanetetranoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5] decan-2,4-dione, the condensate of N,N-bis(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetra-methylpiperidyl)-1,3,5-triazine and 1,2-bis(3-aminopropylamino) ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]-decane-2,4-dione, 3-dodecyl-1-(2,2,6,6-tetramethyl-4-piperidyl)pyrrolidin-2, 5-dione, 3-dodecyl-1-(1,2,2,6,6-pentamethyl-14-piperidyl)-pyrrolidine-2,5-dione, a mixture of 4-hexadecyloxy- and 4-stearyloxy-2,2,6,6-tetramethylpiperidine, the condensate of N,N'-bis(2,2,6,6-tetramethyl-4-piperidyl)hexamethylenediamine and 4-cyclohexylamino-2,6-dichloro-1,3,5-triazine, the condensate of 1,2-bis(3-aminopropylamino)ethane and 2,4,6-trichloro-1,3,5-triazine and 4-butylamino-2,2,6,6-tetramethylpiperidine (CAS reg. No. [136504-96-6]); (2,2,6,6-tetramethyl-4-piperidyl)-n-dodecylsuccinimide, (1,2,2,6,6-pentamethyl-4-piperidyl)-n-dodecylsuccinimide, 2-undecyl-7,7,9,9-tetramethyl-1-oxa-3,8-diaza-4-oxo-spiro[4,5] decane, the reaction product of 7,7,9,9-tetramethyl-2-cycloundecyl-1-oxa-3,8-diaza-4-oxospiro[4,5]decane and epichlorohydrin without being limited thereto.

Examples of insect repellants which can be used in body care products according to the invention are for example N,N-diethyl-m-toluamide, 1,2-pentanediol or insect repellant 3535.

Examples of self tanning ingredients are e.g. dihydroxyacetone and/or erythrulose or dihydroxy acetone and/or dihydroxyacetone precursors as described in WO 01/85124 and/or erythrulose.

Examples of skin whitening ingredients are for example vitamin C, sodium ascorbyl phosphate and magnesium ascorbyl phosphate.

Examples of deodorizing active ingredients which come into consideration are antiperspirants such as aluminum chlorohydrates, aluminum hydroxyacetates and acidic aluminum/zirconium salts. Esterase inhibitors may be added as further deodorizing active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odor formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Other antibacterials which could be present are chitosan, phenoxyethanol and chlorhexidinegluconate-5-chloro-2-(2,4-dichlorophenoxy)-phenol (Triclosan, Irgasan, Ciba Specialty Chemicals Inc.).

Examples of anti-dandruff agents which may be used are dimbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Examples of preservatives include Methyl-, Ethyl-, Propyl-, Butylparabens, Benzalkonium chloride, 2-Bromo-2-nitro-propane-1,3-diol, Dehydroacetic acid, Diazolidinyl Urea, 2-Dichlorobenzyl alcohol, DMDM hydantoin, Formaldehyde solution, Methyldibromoglutaronitrile, Phenoxyethanol, Sodium Hydroxymethylglycinate, Imidazolidinyl Urea, Triclosan and further substance classes listed in the following reference: K. F. De Polo-A short textbook of cosmetology, Chapter 7, Table 7-2, 7-3, 7-4 and 7-5, p 210-219.

Typical examples of bacteria-inhibiting agents are preservatives that have a specific action against gram-positive bacteria, such as 2,4, 4'-trichloro-2'-hydroxydiphenyl ether, chlorhexidine (1,6-di (4-chlorophenyl-biguanido) hexane) or TCC (3,4, 4'-trichlorocarbanilide). A large number of aromatic substances and ethereal oils also have antimicrobial properties. Typical examples are the active ingredients eugenol, menthol and thymol in clove oil, mint oil and thyme oil. A natural deodorizing agent of interest is the terpene alcohol farnesol (3,7,11-tri-methyl-2, 6,10-dodecatrien-1-ol), which is present in lime blossom oil. Glycerolmonolaurate has also proved to be a bacteriostatic agent. The amount of the additional bacteria-inhibiting agents present is usually from 0.1 to 2 wt. %, based on the solids content of the preparations.

The present stabilizer composition is especially suitable for stabilizing body care products, in particular:

skin-care preparations, e.g. skin-washing and cleansing preparations in the form of tablet-form or liquid soaps, sapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils; body oils, body lotions, body gels; skin protection ointments;

cosmetic personal care preparations, e.g. facial make-up in the form of day creams or powder creams, face powder (loose or pressed), rouge or cream make-up, eye-care preparations, e.g. eye shadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, pre-shave preparations for dry shaving, aftershaves or aftershave lotions;

scent or fragrance preparations, e.g. scent, fragrance and/or odorant ingredient containing preparations such as perfumes, eau de Colognes, eau de toilettes, eau de perfumes, eau de toilettes, perfume oils or perfume creams;

cosmetic hair-treatment preparations, e.g. hair-washing preparations in the form of shampoos and conditioners, hair-care preparations, e.g. pre-treatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or chamomile;

dentifrices, in particular tooth creams, toothpastes, mouth-washes, mouth rinses, anti-plaque preparations and cleansing agents for dentures;

decorative preparations, in particular lipsticks, nail varnishes, eye shadows, mascaras, dry and moist make-up, rouge, powders, depilatory agents and suntan lotions cosmetic formulations containing active ingredients, in particular hormone preparations, vitamin preparations, vegetable extract preparations and antibacterial preparations.

The final formulations listed may exist in a wide variety of presentation forms, for example in the form of liquid preparations, as a W/O, O/W, OIW/O, W/O/W or PIT emulsion and all kinds of micro emulsions, in the form of a gel, —in the form of an oil, a cream, milk or lotion, in the form of a stick, in the form of a spray (spray with propellant gas or pump-action spray) or an aerosol, —in the form of a foam, or in the form of a paste.

Of special importance as cosmetic preparations for the skin according to the invention are colorant, dye, active ingredient, scent, fragrance or mixtures thereof containing preparations, such as sun milks, lotions, creams, wipes, oils, sun blocks or tropicals, pre-tanning preparations or after-sun preparations, also skin-tanning preparations, for example self-tanning creams.

Of special importance as cosmetic preparations for the hair are the above-mentioned preparations for hair treatment, especially hair-washing preparations in the form of shampoos, hair conditioners, hair-care preparations, e.g. pre-treatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

The present stabilizing composition is also suited to stabilize photosensitive colorants, dyes, scents, fragrances, active ingredients or mixtures thereof used in household cleansing and treatment agents, for example in laundry products and fabric softeners, non-detergent based fabric products, liquid cleansing and scouring agents, glass detergents, neutral cleaners (all-purpose cleaners), acid household cleaners (bath), bathroom cleaners, for instance in washing, rinsing and dishwashing agents, kitchen and oven cleaners, clear rinsing agents, dishwasher detergents, shoe polishes, polishing waxes, floor detergents and polishes, metal, glass and ceramic cleaners, textile-care products, rug cleaners and carpet shampoos, agents for removing rust, color and stains (stain remover salt), furniture and multipurpose polishes and leather and vinyl dressing agents (leather and vinyl sprays) and air fresheners.

The present invention also concerns the stabilization photosensitive colorants, dyes and/or fragrances and/or active ingredients in home care and fabric care products such as drain cleaners, disinfectant solutions, upholstery cleaners, automotive care products (e.g., to clean and/or polish and protect paint, tires, chrome, vinyl, leather, fabric, rubber, plastic and fabric), degreasers, polishes (glass, wood, leather, plastic, marble, granite, and tile, etc.), and metal polishes and cleaners. Antioxidants are suitable to protect fragrances in above products as well as in dryer sheets.

The present invention also relates to the stabilization of photosensitive colorants, dyes, scents, fragrances, active ingredients or mixtures thereof in home care products such as candles, gel candles, air fresheners and fragrance oils (for the home).

The stabilizers of the present invention may be employed in fabric treatment that takes place after use of the fabric, referred to as fabric care. Such treatments include laundering, which uses detergents, laundry aids and/or fabric conditioner, and the application of non-detergent based fabric care products, such as spray-on products. When employed in this fashion, the present stabilizers are intended for deposition onto the fabric and used to protect the fabric, colorants and fragrances associated with said these fabrics from environmental damage.

The following examples are provided to further illustrate the present invention. These examples are illustrative only and are not intended to limit the scope of the invention in any way.

The following stabilizing composition has been employed in the examples:
15 wt. % of 4,4'-Methoxy-tert.butyldibenzoylmethane (avobenzone, PARSOL® 1789)
60 wt. % of 2-Ethylhexyl 2-cyano-3,3-diphenylacrylate (Octocrylene, PARSOL® 340)
23 wt. % of Homomethylsalicylate (Homosalate®, Parsol HMS)
and 2 wt. % of natural tocopherol (Dermofeel® Toco 70 by drstraetmans).

EXAMPLE 1

Solubility

An often occurring problem in the stabilization of colorants, dyes, fragrances and active ingredients is the solubility respectively the crystallization of the stabilizer/stabilizing composition in the final product form. This results in an unwanted precipitation or turbidity of the end product which is highly undesirable.

Thus, the solubility of the stabilization composition according to the invention in a mixture of water and ethanol (96%) of 53.9/46 wt. % as commonly found in perfumes was compared to a widely used stabilizer of the benzophenone group.

| Stabilizer | 0.1 wt. % stabilizing composition according to the invention | 0.1 wt. % Benzophenon-3 | 0.1 wt. % Benzophenon-2 |
|---|---|---|---|
| Appearance | Clear | Turbid | Precipitate |

The stabilizing composition according to the invention remains dissolved and the solution clear whereas the reference samples are cosmetically not acceptable due to turbidity and precipitation.

EXAMPLE 2

Color and/or Fragrance Stabilization

A: Color and Fragrance Stabilization in an Eau de Toilet

An Eau de toilet consisting of a mixture of 10 wt. % perfume base (Pö AON), 19.9 wt. % of water, 70 wt. % of ethanol (96%) colorized with 0.74 ppm Jaune De Quinoleine 70% (CI 47005) and 0.74 ppm FD&C Red 40 WO93 (CI 16035) and stabilized with 0.1 wt. % of a stabilizing composition according to the invention was irradiated with 80MED. Afterwards the color change was measured with a Minolta CM-3600 and compared to a non-irradiated sample. Additionally, the odor change was determined by olfactive comparison of the samples.

Results

| LAB - value | Non-irradiated | Sample 1 | Reference |
|---|---|---|---|
| L | 89.44 | 89.21 | 95.47 |
| A | 9.23 | 8.87 | −4.61 |
| b | 16.23 | 16.94 | 13.41 |

As can be seen from the results, almost no color change occurs within the sample containing the stabilizing composition, whereas a significant color change is observed within the reference. Also, no olfactive change could be detected within the sample containing the stabilizing composition, whereas a significant off-odor was detected within the reference sample.

B: Color Stabilization in a Liquid Soap

Basic formulation of the liquid soap:

| INCI | Wt. % |
|---|---|
| Sodium Laureth Sulfate | 40.00 |
| Cocamidopropyl Betaine | 10.00 |
| Lauryl Glucoside | 5.00 |
| PEG-7 Glyceryl Cocoate | 3.00 |
| Phenoxyethanol; methylparaben; butylparaben; ethylparaben; propylparaben | 0.60 |
| Polyquaternium-10 | 0.20 |
| Panthenol | 0.40 |
| Disodium EDTA | 0.10 |
| Aqua | 37.3 |
| Tocopheryl Acetate | 0.30 |
| PEG-40 Hydrogenated Castor Oil | 2.00 |
| Sodiumchloride | 1.00 |
| Colorant as indicated below | 0.01 |
| Stabilizing composition according to the invention | 0.10 |

The liquid soaps containing different colorants were irradiated with 100 MED and the color was determined visually according to Tints; PANTONE Color Tint Selector, The PANTONE Library of Color.

Green liquid soap colored with 0.9 ppm Green vent W 7003 (CI 61570)

| | Blank Non irradiated | Blank Irradiated | 0.1 wt. % Benzo-phenone-4 Irradiated | 0.1 wt. % stabilizing composition according to the invention Irradiated |
|---|---|---|---|---|
| Color Index | Pantone 367C 70% Tint | Pantone 3415C 10% Tint | Pantone 367C 70% Tint | Pantone 367C 70% Tint |

Blue liquid soap colored with FD&C Blue 1 W 092 (CI 42090)

| | Blank Non irradiated | Blank Irradiated | 0.1 wt. % Benzo-phenone-1 Irradiated | 0.1 wt. % stabilizing composition according to the invention Irradiated |
|---|---|---|---|---|
| Color Index | Pantone 3125C 50% Tint | Pantone 3105C 10% Tint | Pantone 3125C 50% Tint | Pantone 3125C 50% Tint |

Violet liquid soap colored 3.1 ppm Vert Turquise W 7003 (CI 61570) and 0.5 ppm FD&C Red 40WO93 (CI 16035)

|  | Blank Non irradiated | Blank Irradiated | 0.1 wt. % Benzo-phenone-1 Irradiated | 0.1 wt. % stabilizing composition according to the invention Irradiated |
|---|---|---|---|---|
| Color Index | Pantone 494C 70% Tint | Pantone 4685C 10% Tint | Pantone 495C 30% Tint | Pantone 494C 70% Tint |

As can bee seen from the results shown, the stabilization composition of the invention effectively inhibits the degradation of the colorants. This stabilization effect is equal or better compared to a market standards, benzophenone-4 and benzophenone-1.

EXAMPLE 3

| Shower gel | |
|---|---|
| INCI | wt. % |
| Aqua (water) | Ad to 100 |
| Sodium Laureth Sulfate | 12.90 |
| Cocamidopropyl Betaine | 2.500 |
| Potassium Cocoyl Hydrolized Collagen | 1.500 |
| Sodium Chloride | 1.000 |
| Perfume oil | 1.000 |
| Hydrolized Collagen | 0.900 |
| Decyl Glucoside | 0.900 |
| Polyquaternium 10 | 0.200 |
| Propylene Glycol | 0.180 |
| 5-Bromo-5-Nitro-1,3-Dioxane | 0.020 |
| Chinolingelb E 104 1% solution | 0.010 |
| Stabilizing composition according to the invention | 0.100 |

EXAMPLE 4

| Hair styling spray | |
|---|---|
| INCI | wt. % |
| Alcohol, anhydrous | Ad to 100 |
| Octylacrylamide/acrylate/butylaminoethylmethacrylate copolymer | 2.50 |
| Hydroxypropyl cellulose | 0.50 |
| Aminomethylpropanol | 0.50 |
| Perfume oil | 0.200 |
| Stabilizing composition according to the invention | 0.100 |

The hydroxypropyl cellulose is first dissolved in half of the alcohol and is subsequently charged with aminomethylpropanol. The other components, with exception of the acrylate resin, are dissolved in alcohol and this solution is added under agitation to the hydroxypropyl cellulose followed by the addition of the acrylate resin.

EXAMPLE 5

| Protective Styling Hair Mousse | |
|---|---|
| INCI | wt. % |
| Aqua (water) | Ad 100 |
| Polyquaternium-4 | 2.00 |
| Cocamidopropylamine Oxide | 0.40 |
| PEG-12 Dimethicone | 0.20 |
| Propylene Glycol & Diazolidinyl Urea & Methylparaben & Propylparaben | 1.00 |
| Perfume oil | 0.20 |
| Propane/Butane | 10.00 |
| Stabilizing composition according to the invention | 0.10 |

Add the ingredients in the order shown under agitation. Afterwards, charge in adequate containers with propane/butane.

EXAMPLE 6

| Lip Balm | |
|---|---|
| INCI | wt. % |
| Dimethicone | 5.00 |
| Octyldodecanol | 23.50 |
| *Ricinus Communis* (Castor) Seed Oil | 22.00 |
| Caprylic/Capric Triglyceride | 18.00 |
| Bis-Diglyceryl Polyacyladipate-2 | 7.00 |
| Tribehenin | 2.00 |
| *Copernicia Cerifera* (Carnauba) Wax | 8.00 |
| Beeswax | 10.00 |
| Tocopheryl Acetate | 2.00 |
| *Simmondsia Chinensis* (Jojoba) Seed Oil | 1.00 |
| Bisabolol | 0.70 |
| Panthenol | 0.30 |
| Parfume oil | 0.30 |
| Stabilizing composition according to the invention | 0.20 |

Heat all ingredients except the perfume oil and the stabilizing composition to 85° C. while stirring. When homogenous add perfume oil and stabilizing composition according to the invention. Cool while mixing.

EXAMPLE 7

| Make up/Foundation/Day Cream | | |
|---|---|---|
| | INCI | wt. % |
| A) | Octyldodecanol | 4.00 |
| | Glyceryl Stearate SE | 4.50 |
| | Talc | 1.00 |
| | Titanium Dioxide | 6.00 |
| | Iron Oxides | 0.80 |
| | *Ricinus Communis* (Castor) Seed Oil | 8.00 |
| | Sorbitan Sesquioleate | 0.50 |
| | Steareth-2 | 0.50 |
| | Tocopheryl Acetate | 2.00 |
| | Disodium EDTA | 0.10 |
| | BHT | 0.05 |
| | Phenoxyethanol & Methylparaben & Ethylparaben & Butylparaben & Propylparaben & Isobutylparaben | 0.60 |
| | Potassium Cetyl Phosphate | 2.00 |

-continued

| Make up/Foundation/Day Cream | | |
|---|---|---|
| | INCI | wt. % |
| B) | Aqua (water) | ad 100 |
| | Propylene Glycol | 5.00 |
| | Carbomer | 1.00 |
| C) | Cyclomethicone | 4.00 |
| | Dimethicone | 5.00 |
| | Perfume oil | 0.20 |
| | Stabilizing composition according to the invention | 0.10 |

Heat part A) to 85° C. while stirring. When homogeneous, add part B) pre-heated to 75° C. While mixing, cool to ambient temperature, (not above 25° C.) and add part C) under stirring. Pass trough a 3-Rollmill.

EXAMPLE 8

| Shampoo for greasy hair | |
|---|---|
| INCI | wt. % |
| Sodium myreth sulfate | 50.00 |
| TEA abietoyl collagen hydrolysate | 3.50 |
| Laureth-3 | 3.00 |
| Phosphonomethylchitosan sodium salt | 0.01 |
| Aqua (water) | Ad 100 |
| Colorant (D&C Red No. 33) | 0.20 |
| Parfume oil | 0.15 |
| Stabilizing composition according to the invention | 0.20 |

The components are mixed with stirring at RT until they are completely dissolved.

EXAMPLE 9

| Green colored glass detergent | |
|---|---|
| INCI | wt. % |
| Anionic/amphoteric surfactants (Lumurol RK) | 0.70 |
| Butyl glycol | 5.00 |
| Isopropanol | 20.00 |
| Colorant (D&C Green No. 2) | 0.05 |
| Aqua (water) | Ad 100 |
| Perfume oil | 4.00 |
| Stabilizing composition according to the invention | 0.20 |

The components are mixed with stirring at RT until a homogenous mixture is obtained. Excellent results are achieved.

EXAMPLE 10

| After Shave Balm | |
|---|---|
| INCI | wt. % |
| Aqua (water) | ad. 100 |
| Acohol denat. | 25.00 |
| Cetearyl ethylhexanoate | 5.00 |
| Propylene glycol | 3.00 |

-continued

| After Shave Balm | |
|---|---|
| INCI | wt. % |
| Glyerin | 3.00 |
| Fragrance | 2.50 |
| Tocopheryl acetate | 1.50 |
| Panthenol | 1.00 |
| Carbomer | 0.30 |
| Acrylates/C10-30 alkyl acrylate crosspolymer | 0.30 |
| Disodium EDTA | 0.10 |
| PEG-40 hydrogenated castor oil | 2.00 |
| Preservative | 1.00 |
| Sodium hyaluronate | 0.01 |
| Sodium hydroxide | q.s. |
| FD&C Blue No 1 | 0.01 |
| CI 42090 | 0.01 |
| Stabilizing composition according to the invention | 0.05 |

The components are mixed with stirring at RT until a homogenous mixture is obtained. Excellent results are achieved.

EXAMPLE 11

| Aftershave lotion | |
|---|---|
| INCI | wt. % |
| Alcohol denat. | 32.00 |
| Aqua (water) | ad. 100 |
| Fragrance | 1.50 |
| Propylene glycol | 2.00 |
| PEG-40 hydrogenated castor oil | 2.50 |
| Linalool | 0.01 |
| Limonene | 0.01 |
| Ethylhexyl salicylate | 0.01 |
| Citronellol | 0.20 |
| Citral | 0.10 |
| CI 60730 | 0.001 |
| CI 42090 | 0.003 |
| Stabilizing composition according to the invention | 0.10 |

The components are mixed with stirring at RT until a homogenous mixture is obtained. Excellent results are achieved.

EXAMPLE 12

| Aftershave Lotion mit Carotene | |
|---|---|
| INCI | wt. % |
| Alcohol denat. | 30.00 |
| Aqua (water) | Ad. 100 |
| Fragrance | 2.00 |
| Glycerine | 3.00 |
| Panthenol | 0.50 |
| Bisabol | 0.10 |
| BHT | 0.10 |
| Stabilizing composition according to the invention | 0.10 |
| Carotene | 0.02 |

The components are mixed with stirring at RT until a homogenous mixture is obtained. Excellent results are achieved.

EXAMPLE 13

| Perfume EDT | |
|---|---|
| INCI | wt. % |
| Alcohol denat., | 82.00 |
| Aqua (water) | Ad. 100 |
| Perfume oil | 17.50 |
| Stabilizing composition according to the invention | 0.15 |
| ext. D&C violet no. 2 (CI 60730) | 0.023 |

The components are mixed with stirring at RT until a homogenous mixture is obtained. Excellent results are achieved.

EXAMPLE 14

| Nail varnish | |
|---|---|
| INCI | wt. % |
| Methyl ethyl ketone | 36.00 |
| Isopropyl alcohol | 28.00 |
| Aqua (water) | Ad. 100 |
| Ethyl acetate | 20.00 |
| Tocopheryl acetate | 0.05 |
| Fragrance | 0.50 |
| Stabilizing composition according to the invention | 0.10 |
| CI 42090 | 0.01 |

The components are mixed with stirring at RT until a homogenous mixture is obtained. Excellent results are achieved.

EXAMPLE 15

| Eau de Toilette | |
|---|---|
| INCI | wt. % |
| Alcohol | 55.00 |
| Perfume oil | 8.00 |
| Water | Ad. 100 |
| Stabilizing composition according to the invention | 0.15 |
| FD&C Blue No. 1 1% | 0.001 |
| FD&C Red No. 40 1% | 0.030 |
| FD&C Yellow No. 5 1% | 0.100 |

The components are mixed with stirring at RT until a homogenous mixture is obtained. Excellent results are achieved.

EXAMPLE 16

| Anti Dandruff Shampoo | |
|---|---|
| INCI | wt. % |
| Water | ad 100 |
| Ammonium laureth sulphate | 35.00 |
| Ammonium lauryl sulphate | 15.00 |
| Glycol disearate | 1.00 |
| Dimethicone | 1.00 |
| Cetyl alcohol | 0.50 |
| Cocamide MEA | 3.00 |
| ZPT | 1.00 |
| Guar hydroxipropyltrimonium chloride | 0.20 |
| Hydrogenated polydecene | 1.00 |
| Polyquaternium 10 | 0.10 |
| PEG 7m | 0.50 |
| Trimethylpropane tricaprylate/tricaprate | 1.00 |
| Preservative | q.s. |
| Fragrance | 0.30 |
| E 104, E 110, E 132 | 0.02 |
| Stabilizing composition according to the invention | 0.10 |

EXAMPLE 17

| Conditioner Shampoo | |
|---|---|
| INCI | wt. % |
| Water | Ad 100 |
| Sodium laureth sulphate | 25.00 |
| Cocamidopropyl betaine | 5.00 |
| Sodium chloride | 2.50 |
| Glycol distearate | 1.00 |
| Glycerin | 2.00 |
| Dimethiconol | 0.50 |
| Fragrance | 0.50 |
| coco-glucoside | 3.00 |
| carbomer | 0.10 |
| arginine | 0.05 |
| glyceryl oleate | 0.05 |
| glyceryl stearate | 1.00 |
| guar hydroxypropyltrimonium chloride | 0.10 |
| panthenol | 1.00 |
| disodium EDTA | 0.05 |
| preservative | q.s. |
| hydrolyzed keratin | 0.10 |
| citric acid/sodium hydroxide | q.s |
| Stabilizing composition according to the invention | 0.10 |
| E 102, E 110, FD&C blue | 0.01 |

EXAMPLE 18

| Shampoo with plant extracts | |
|---|---|
| INCI | wt. % |
| Aqua | Ad 100.00 |
| Sodium laureth sulfate | 25.00 |
| Lauryl glucoside | 10.00 |
| Cocamidopropyl betaine, | 5.00 |
| Propylene glycol | 2.0 |
| Fragrance | 1.25 |
| Sodium citrate | 0.25 |
| Sodium benzoate | 0.20 |

Shampoo with plant extracts

| INCI | wt. % |
| --- | --- |
| Panthenol | 1.00 |
| Sodium formate | 0.20 |
| Polyquaternium-10 | 0.20 |
| Hydroxypropyl guar hydroxypropyltrimonium chloride | 0.05 |
| PEG-35 castor oil | 1.00 |
| Maris sal | 1.25 |
| Polysorbate 20 | 1.00 |
| Tocopheryl acetate | 0.20 |
| *Prunus armeniaca* | 0.20 |
| *Echinacea purpurea* | 0.05 |
| Retinyl palmitate | 0.05 |
| Tocopherol | 0.05 |
| Linoleic acid | 0.20 |
| Preservative | 1.00 |
| Stabilizing composition according to the invention | 0.20 |
| CI77891 | 0.02 |

EXAMPLE 19

Shine Shampoo

| INCI | wt. % |
| --- | --- |
| Aqua | q.s. |
| Sodium laureth sulfate | 15.00 |
| Disodium cocoamphodiacetate | 15.00 |
| Sodium chloride | 2.00 |
| Glycol distearate | 1.00 |
| Cocamidopropyl PYL betaine | 2.00 |
| Laurdimonium hydroxypropyl hydrolyzed wheat rotein, | 1.00 |
| PEG-12 dimethicone | 1.00 |
| Guar hydroxypro pyltrimonium chloride | 0.05 |
| Hydrolyzed wheat protein | 0.20 |
| Laureth-4 | 1.00 |
| PEG-7 glyceryl, cocoate | 2.00 |
| Hydrogenated castor oil | 1.00 |
| Laureth-2 | 0.50 |
| PEG-55 propylene glycol oleate, | 2.00 |
| Propylene glycol | 2.00 |
| Mica | 0.20 |
| Citric acid | 0.01 |
| Fragrance | 1.00 |
| E 110, E 104, E 122 | 0.05 |
| Stabilizing composition according to the invention | 0.20 |

The invention claimed is:

1. A method for the stabilization of colorants, dyes, scents, fragrances, active ingredients or mixtures thereof in liquid body care products and liquid household products which method comprises adding to a body care product or household product an effective stabilizing amount of a liquid stabilizing composition comprising 12-17 wt. % of 4,4'-methoxy-tert.butyldibenzoylmethane,
55-65 wt. % of 2-cyano-3,3-diphenylacrylate,
18-25 wt. % homomethylsalicylate,
and, optionally, 0.5-5 wt. % mixed or natural tocopherol,
and, further optionally, other cosmetic additives
wherein the sum of the ingredients is 100%.

2. The method according to claim 1 wherein the active ingredient is selected from the group consisting of: vitamins, carotenoids, vegetable extract, antibacterials, ubiquinones, phenols, polyphenols and flavanoids.

3. The method according to claim 1 wherein the effective stabilizing amount is within a concentration range of 0.05-0.5 wt. % based on the total weight of the product.

4. A liquid stabilizing composition comprising
12-17 wt. % 4,4'-methoxy-tert.butyldibenzoylmethane
55-65 wt. % 2-cyano-3,3-diphenylacrylate
18-25 wt. % homomethylsalicylate
and, optionally, 0.5-5 wt. % mixed or natural tocopherol
and, further optionally, other cosmetic additives
wherein the sum of the ingredients is 100%.

5. The stabilizing composition according to claim 4 wherein the 2-cyano-3,3-diphenylacrylate is 2-ethylhexyl 2-cyano-3,3-diphenylacrylate.

6. A body care product or household product containing an effective stabilizing amount of a stabilizing composition according to claim 4.

7. The body care product or household product according to claim 6 wherein the effective stabilizing amount is within a concentration range of 0.05-1 wt. % based on the total weight of the product.

8. The body care product or household product according to claim 7 wherein the effective stabilizing amount is within a concentration range of 0.05-0.5 wt. % based on the total weight of the product.

9. The body care product according to claim 7 which is a perfume or a toilet water.

\* \* \* \* \*